United States Patent [19]

Baiker et al.

[11] Patent Number: 5,935,895
[45] Date of Patent: *Aug. 10, 1999

[54] HETEROGENEOUS CATALYSTS

[75] Inventors: Alfons Baiker, Glattbrugg; Dominique Dutoit, Egliswil; Remo Hutter, Kriessern, all of Switzerland

[73] Assignee: Roche Vitamins Inc., Parsippany, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/809,329

[22] PCT Filed: Sep. 8, 1995

[86] PCT No.: PCT/EP95/03530

§ 371 Date: Mar. 18, 1997

§ 102(e) Date: Mar. 18, 1997

[87] PCT Pub. No.: WO96/09117

PCT Pub. Date: Mar. 28, 1996

[30] Foreign Application Priority Data

Sep. 22, 1994 [CH] Switzerland .............................. 2882/94

[51] Int. Cl.$^6$ .............................. B01J 23/00; B01J 20/00; B01J 13/00; C03C 3/00
[52] U.S. Cl. .......................... 502/349; 502/233; 502/236; 502/239; 502/242; 502/405; 502/408; 502/415; 501/12; 516/111
[58] Field of Search ..................... 502/349, 233, 502/236, 242, 239, 405, 408, 415; 501/12; 252/315.01; 516/111

[56] References Cited

U.S. PATENT DOCUMENTS

| | | | |
|---|---|---|---|
| 3,829,392 | 8/1974 | Wulff | 252/430 |
| 3,923,843 | 12/1975 | Wulff | 260/348.5 |
| 4,432,956 | 2/1984 | Zarzycki et al. | 423/338 |
| 4,478,987 | 10/1984 | Fanelli et al. | 502/132 |
| 4,550,093 | 10/1985 | Fanelli et al. | 502/235 |
| 4,619,908 | 10/1986 | Cheng et al. | 502/235 |
| 4,717,708 | 1/1988 | Cheng et al. | 502/235 |
| 5,008,219 | 4/1991 | Hara | 501/12 |
| 5,019,146 | 5/1991 | Hara | 65/18.1 |
| 5,558,849 | 9/1996 | Sharp | 502/233 |

Primary Examiner—Mark L. Bell
Assistant Examiner—Patricia L. Hailey
Attorney, Agent, or Firm—George W. Johnston; Dennis P. Tramaloni

[57] ABSTRACT

A silica-titania mixed oxide catalyst and its method of manufacture is disclosed. Such catalysts can be used especially to catalyze the epoxidation of olefinically unsaturated compounds with organic hydroperoxides.

12 Claims, No Drawings

HETEROGENEOUS CATALYSTS

Processes are known according to which olefin oxides (epoxides) are manufactured by reacting corresponding olefins with organic hydroperoxides using certain heterogeneous catalysts. Suitable catalysts which are effective for this purpose are oxides or hydroxides of, for example, titanium or molybdenum, which are chemically combined with silicon oxides, e.g. silicon dioxide (silica). By treating such heterogeneous catalysts, e.g. titanium dioxide (titania) chemically combined with silica, with an organic silylating reagent, e.g. an organic halosilane, at elevated temperatures there is achieved according to U.S. Pat. Nos. 3,829,392 and 3,923,843 a better productivity, with the selectivity of the epoxidation being improved and the tendency of the organic hydroperoxide to decompose to undesired byproducts under the influence of the heterogeneous catalyst being reduced.

As is known, disadvantages of heterogeneous catalysts of the above type in comparison to homogeneous catalysts, e.g. molybdenum compounds, are the relatively low activity and somewhat lower selectivity. The known high reactivity of organic hydroperoxides, especially in the epoxidation of olefins, and the general tendency of these hydroperoxides to decompose in the presence of a variety of catalytic materials to undesired byproducts has motivated the search for more selective and more active catalysts for the epoxidation of olefins and also for other oxidations.

The object of the present invention was to provide silica-titania mixed oxide catalysts which on the one hand exhibit an increased activity in oxidations with organic hydroperoxides, especially in epoxidations of olefins, and on the other hand are at least equal to known catalysts with respect to selectivity and the stability of titanium in the solid matrix of the mixed metal oxides. In order to fulfill these goals efforts were made to achieve an intermixing of the silicon and titanium components, each being bridged via an oxygen atom, as atomically as possible, i.e. the provision of as many as possible bonds of the Si—O—Ti type in a highly cross-linked structure; a specific surface area which is as high as possible; a pore volume which is as large as possible; as well as not only a dispersion of the titanium which is as high as possible, but also its accessibility at the surface. These characteristics are of great significance for catalysis in the field of fine chemicals. In particular, a large pore volume is necessary in order that the relatively large molecules generally encountered in fine chemistry can enter into the porous catalyst.

It has surprisingly been found that the desired silica-titania mixed oxide catalysts can be manufactured by producing a sol under acidic or basic hydrolysis conditions from optionally pre-hydrolyzed silicon alkoxide and from titanium alkoxide, the hydrolyzability of which is reduced by chelate formation, gelling and ageing this sol, drying the thus-produced aged gel by extraction of the solvent used in the production of the sol and of the alcohol produced in the hydrolysis with super-critical carbon dioxide and, if desired, calcinating the aerogel resulting therefrom at temperatures up to 1000° C. in a gas stream containing oxygen. The present invention is concerned with a thus-manufacturable catalyst, the respective process for the manufacture of the catalyst, and the use of such catalysts in the epoxidation of olefinically unsaturated compounds with organic hydroperoxides.

U.S. Pat. No. 4,176,089 teaches the preparation of mixed silica-titania materials, suitable as catalysts or catalyst supports, by mining silicon and titanium alkoxides and an organic diluent, adding the resulting premixed alkoxides to a hydrolysis medium of water and a solvent to form a silica-titania precipitate, separating this from the hydrolysis medium, drying and calcinating the precipitate and recovering the resulting high surface area, low bulk density silica-titania product. However, there is no disclosure in this U.S. patent specification of reducing the hydrolyzability of the titanium alkoxide by chelate formation or of extracting the solvent and alcohol with supercritical carbon dioxide. Although the problem of the slower hydrolysis rate of silicon alkoxides compared to titanium alkoxides is recognized, the problem is only believed to be solved by using an alcohol as the diluent, whereby the solvation of the titanium alkoxide therein retards its rate of hydrolysis and/or the formation of titanium alkoxide acids catalyses the hydrolysis of the silicon alkoxides.

European Patent Publication 492,697 teaches a wide range of catalytically active gels of a silica matrix within which one or more metal oxides, e.g. titanium oxide, are dispersed. Said gels are obtained by heating an aqueous solution of a tetraalkyl ammonium hydroxide, a soluble silicon compound, e.g. a tetraalkyl silicate, and soluble salt(s) or acid(s) of the other metal(s), e.g. tetraethyl orthotitanate, to cause gelling, drying the gel and calcinating the dried gel in an inert and then an oxidizing atmosphere. The problem of different hydrolysis rates of the metal alkoxides is not mentioned, nor any means of e.g. reducing the hydrolyzability of titanium alkoxide or of extracting solvent and alcohol from the gel. Furthermore, the level of epoxidation (of 1-octane with tert. butyl hydroperoxide: see Example 16a) achieved with a titanium silica gel is very low.

One feature of the catalyst manufacturable in accordance with the invention is that the titanium alkoxide used for its manufacture can be hydrolyzed less readily than normal, namely by chelate formation. The titanium alkoxide itself is preferably one of the formula $Ti(OR^1)_4$, wherein each $R^1$ signifies $C_{1-4}$-alkyl, and is most preferably tetraisopropyl orthotitanate. Suitable ligands for the chelate formation are, inter alia, acetylacetone, glycols, monomethyl maleate and dibutyl phosphate, especially acetylacetone (denoted for brevity as "acac"). The ligand to titanium alkoxide molar ratio attained after chelate formation depends on the reaction conditions under which the chelate formation to the so-called complexed titanium alkoxide precursor is effected. This chelate formation can be carried out according to methods known per se, generally by heating a solution of the titanium alkoxide and the ligand in a suitable solvent for several hours and, after completion of the reaction, cooling the solution and removing the solvent by evaporation under reduced pressure. A typical example of such a chelate formation is that from a titanium alkoxide, e.g. tetraisopropyl orthotitanate, and acetylacetone in a molar ratio between about 1:2 and about 3:1 in an alcohol, conveniently in the alkanol $R^1OH$ corresponding to the titanium alkoxide $Ti(OR^1)_4$, at the reflux temperature of the reaction mixture. The molar concentration of the titanium alkoxide in the alcohol conveniently lies in the range of about 0.1 to about 2.0M and the heating normally takes about 0.5 to about 6 hours. The subsequent cooling as well as the evaporation of the solvent—and thus the isolation of the thus-produced complexed titanium alkoxide precursor—requires no special critical conditions.

The sol is firstly produced from the complexed titanium alkoxide precursor ("titanium alkoxide, the hydrolyzability of which is reduced by chelate formation"), preparable in the above manner, and an optionally pre-hydrolyzed silicon alkoxide by acid- or base-catalysed hydrolysis of the complexed titanium alkoxide precursor in the same hydrolysis medium in which the optionally pre-hydrolyzed silicon alkoxide is present. Where the latter is not pre-hydrolyzed, a concomitant hydrolysis of the two alkoxides is effected.

The silicon alkoxide is preferably one of the formula $Si(OR^2)_4$, wherein each $R^2$ signifies $C_{1-4}$-alkyl, and is most preferably tetramethoxysilane. Where this is employed in pre-hydrolyzed form in the production of the sol, the separate hydrolysis is conveniently carried out by homogenizing the silicon alkoxide in a suitable solvent, especially a $C_{1-4}$-alkanol, preferably isopropanol, for several minutes, combining the homogenized solution with an aqueous-alcoholic solution of a suitable acid or base and slightly heating the resulting solution of the silicon alkoxide and the acid or base in an aqueous alcohol for several minutes to several hours. The concentration of the silicon alkoxide in the alcoholic solution to be homogenized conveniently lies in the range of about 5M to about 10M, preferably of about 6M to about 7M, and the homogenization is conveniently effected in the temperature range of about 20° C. to about 60° C., preferably at room temperature, by vigorous stirring. A homogenized solution is normally obtained within about 5 minutes. The acid or base which catalyzes the hydrolysis is conveniently an inorganic (mineral) acid, preferably hydrochloric acid or, respectively, an alkali metal hydroxide such as sodium hydroxide or potassium hydroxide, preferably the former. The convenient concentration of acid or base in the aqueous-alcoholic solution will, of course, depend on the respective acid or base which is used, on the water:alcohol ratio by volume and on the alcohol. In general, the concentration lies in the range of about 0.2M to about 5M and the ratio lies in the range of about 2:1 to about 1:3 (water:alcohol). The alcohol is conveniently a $C_{1-4}$-alkanol, preferably the same alkanol which is used for the solution of the silicon alkoxide. After both solutions have been prepared they are combined, preferably at room temperature, and the combined solution is subsequently heated while stirring, conveniently at temperatures between about 40° C. and about 70° C. In this manner the hydrolysis ("pre-hydrolysis") of the silicon alkoxide is completed within about 20 hours, although the the hydrolysis period can be as brief as about 30 minutes. The amounts of solutions to be combined are chosen such that about 0.01 to 1 mol of acid or base is used per mol of silicon alkoxide. In general, the acid-catalyzed hydrolysis of the silicon alkoxide is preferred to its base-catalysed hydrolysis.

When pre-hydrolyzed silicon alkoxide is used, the complexed titanium alkoxide precursor, produced as described above, is conveniently added to the solution, cooled to room temperature, of the pre-hydrolyzed silicon alkoxide, followed by additional aqueous alcohol and optionally still further alcohol. Since the resulting medium already contains acid or base from the preceding silicon alkoxide hydrolysis ("pre-hydrolysis"), the hydrolysis of the complexed titanium alkoxide precursor and thereby the sol formation is initated, whereby a water-cleaving condensation between the hydroxyl groups of the hydrolyzed silicon alkoxide and the newly formed hydroxyl groups of the hydrolyzed complexed titanium alkoxide precursor takes place with the formation of oligomers having Si—O—Ti bonds. The silicon:titanium molar ratio in the hydrolysis medium and in the sol resulting therefrom conveniently lies in the range of about 1:1 to about 70:1, preferably in the range of about 3:1 to about 12:1, and the total molar concentration of silicon and titanium compounds brought together in the hydrolysis medium augmented with water and alcohol conveniently amounts to about 2M to about 10M. The hydrolysis (and resulting sol production) is conveniently effected in the temperature range of about 0° C. to about 60 ° C., preferably at room temperature.

In the case of the aforementioned concomitant hydrolysis of the two alkoxides (without pre-hydrolysis of the silicon alkoxide), the complexed titanium alkoxide precursor, produced as described above, and the silicon alkoxide are conveniently dissolved together in a suitable solvent, especially a $C_{1-4}$-alkanol, preferably isopropanol (usually in the same solvent in which the complexed titanium alkoxide precursor has been produced) and subsequently treated with an aqueous-alcoholic solution of a suitable acid or base. The conditions under which the concomitant hydrolysis is carried out are the same as the above-described conditions for the separate hydrolysis ("pre-hydrolysis") of the silicon alkoxide with respect to the choice and concentration of the acid or base, the concentration of the alkoxide in the hydrolyzing medium, the water:alcohol volume ratio etc. In this case, however, the concomitant hydrolysis is preferably carried out at room temperature. As in the case of the hydrolysis of the complexed titanium alkoxide precursor together with the pre-hydrolyzed silicon alkoxide, likewise described above, the silicon:titanium molar ratio in the hydrolysis medium is conveniently between about 1:1 and about 70:1, preferably between about 3:1 and about 12:1. Likewise analogously to this hydrolysis, the sol formation is also initiated in the present hydrolysis.

Irrespective of whether a pre-hydrolysis is carried out or not, the two hydrolyses or, respectively, the concomitant hydrolysis are preferably catalysed with acid, particularly with hydrochloric acid.

The next step of the process for the manufacture of the catalyst in accordance with the invention comprises gelling and ageing the sol of the preceding step. This is conveniently effected by exposing the sol to a dry inert gas stream for several hours or even days with constant stirring. A suitable inert gas is especially nitrogen or argon, preferably the former on economic grounds, and the throughflow is conveniently effected at a pressure in the range of about 1–2 bar and at temperatures between about 15° C. and about 30° C., preferably at a pressure of about 1 bar and at room temperature. The throughput velocity of the inert gas is conveniently about 1 ml inert gas/g sol/minute. In this manner a sufficient gelling and ageing, which depends, inter alia, on the solvent and titanium content, can be achieved within about 24 hours. However, this can take significantly longer such as, for example, over 200 days: a relatively long gelling and ageing period is not harmful to the aged gel, provided that the gel is not dried out completely, but is not very advisable on technical and economical grounds.

The inert gas stream serves to drive off solvent present in the sol, which is due to the constricting action of the gas. During the gelation the formation of larger, cross-linked polymers from the oligomers present to a great extent in the sol occurs, this being associated with an increased viscosity. The ageing leads to a stabilization of the network.

The subsequent drying (extraction) is effected by exposing the aged gel to supercritical carbon dioxide, i.e. carbon dioxide at temperatures and pressures above its critical temperature of about 31° C. and above its critical pressure of about 73 bar, conveniently at mild temperatures in the range of about 31° C. to about 50° C., preferably of about 35° C. to about 40° C., and at a pressure preferably in the range of about 200 to about 270 bar. The extraction is suitably carried out by slowly introducing the carbon dioxide into a closed vessel in which the aged gel is situated, preferably within 1 to 4 hours, and until the supercritical pressure is achieved and subsequently adjusting a through-flow of carbon dioxide, whereafter the extraction is effected over several hours, conveniently in the range of about 4 to 10 hours. The carbon dioxide ($CO_2$) throughput velocity is conveniently about 50 to about 500 g $CO_2$/l gel/minute. In the same way that the pressure reduction is applied slowly, the pressure reduction to atmospheric pressure which follows the extraction is likewise effected slowly, in this case preferably within 1–6 hours. During this pressure reduction the temperature must still be held in the range of the aforementioned mild temperatures, preferably in the range of about 35° C. to about 40° C., in order to avoid a condensation of the carbon dioxide. After the pressure reduction the mixture is cooled to room temperature and the resulting aerogel is separated and pounded. In this manner the constitution of the wet aged gel is maintained (the capillary forces in the pores produced by liquid/gaseous phase limits must be avoided as much as possible): the liquid situated in the pores is replaced by the supercritical carbon dioxide and the pressure reduced at the critical temperature of the new pore medium. The thus-obtained aerogel has the desired highly cross-linked structure with Si—O—Ti bonds, a specific surface area which is as high as possible, a pore volume which is as large as possible, with the stability being guaranteed by capillary forces (pressures) which are as small as possible, and not only a dispersion of the titanium which is as high as possible, but also its accessibility at the surface. This aerogel itself can already be used as an effective catalyst.

Prior to use as a catalyst the aerogel can be subjected to a calcination in an oxygen-containing gas stream, if desired following a pre-treatment in a dry inert gas at elevated temperature. This pre-treatment is conveniently effected using nitrogen or argon as the inert gas at temperatures of about 100° C. to about 400° C. The throughput velocity of the inert gas suitably lies in the range of about 50 to about 500 ml inert gas/g aerogel/minute. Under such conditions the pre-treatment takes about 30 minutes to about 4 hours, and thereafter the pre-treated aerogel is conveniently cooled to below about 80° C. Then, the calcination is conveniently carried out by heating the aerogel slowly (about 2° C./minute to about 20° C./minute in order to avoid a too rapid combustion of the still present, undesired organic components and thereby a sintering of the aerogel caused by the resulting heat) in a gas stream preferably containing 15 to 25 percent by volume of oxygen until the desired calcination temperature, i.e. a maximum of 1000° C., is achieved, and continuing the calcination at the high temperature for some hours. The gas stream preferably consists of air and conveniently flows with a velocity in the range of about 50 to about 500 ml gas/g aerogel/minute. The entire calcination (heating up as well as heating at the high temperature in the gas stream) normally takes 2 to 12 hours and, after the heating up, is preferably effected at temperatures in the range of about 200° C. to about 600° C. After the subsequent cooling of the calcinated aerogel, which requires no special critical conditions, there is obtained a silica-titania mixed oxide catalyst, which has an intermixing of the silicon and titanium components, each of which is bridged via an oxygen atom, which is as atomic as possible, with a BET (Brunauer-Emmett-Teller) surface area usually between about 500 $m^2$/g and about 800 $m^2$/g and a porosity usually between about 2 nm (mesoporous) and about 60 nm (macroporous). Moreover, the atomic ratio Ti:Si at the surface is generally about 1:19 to about 3:7, preferably about 1:4.

The catalysts in accordance with the invention (and manufacturable according to the process in accordance with the invention) are suitable in general as catalysts in all cases where metal oxide and mixed oxide (heterogeneous) catalysts are usually employed, and especially as catalysts in liquid phase processes for the epoxidation of olefinically unsaturated compounds, e.g. hydrocarbons and carotenoid precursors, by reaction with organic hydroperoxides, e.g. alkyl hydroperoxides and aralkyl hydroperoxides. Use as catalysts in such liquid phase processes represents a further aspect of the present invention. This use is an improvement, because under otherwise identical reaction conditions a distinct increase in activity for the epoxide formation can be established using a catalyst in accordance with the invention in comparison to conventional catalysts produced by impregnating a silica carrier with a titanium-containing solution.

As olefinically unsaturated compounds ("substrates") for the epoxidation there come into consideration in general all organic compounds having at least one aliphatic or alicyclic carbon—carbon double bond, especially those with up to 60 carbon atoms, preferably those with 3 to 20 carbon atoms. Aliphatic compounds having a terminal double bond, e.g. propylene, 1-octene and 1-decene, alicyclic olefins, e.g. cyclohexene and cyclododecene, as well as isoprenoids, e.g. limonene, are amongst the excellently suitable substrates for the epoxidation. Secondary and tertiary alkyl hydroperoxides, especially the latter, e.g. tert.butyl hydroperoxide, and arylalkyl hydroperoxides in which the hydroperoxy group is attached to the benzene ring at the α-carbon atom, e.g. α-methylbenzyl hydroperoxide and cumene hydroperoxide, are preferred organic hydroperoxides.

In general, the catalyzed reaction of the olefinically unsaturated compound with the organic hydroperoxide in the liquid phase is carried out at moderate temperatures and pressures. Especially suitable solvents are hydrocarbons, such as, for example, the hydrocarbon corresponding to the organic hydroperoxide which is used, or simply the olefinically unsaturated compound which is used in excess. The reaction is conveniently effected at temperatures in the range of about 0° C. to about 200° C., preferably of about 25° C. to about 150° C., and at pressures from normal pressure to about 100 bar. With respect to the pressure, the exact ratios are only not critical insofar as the reaction mixture is maintained in the liquid phase. The substrate:hydroperoxide molar ratio should be at least 1:1, with molar ratios of 2:1 to 20:1 being preferred, particularly as the substrate is often also used as the solvent.

The present invention is illustrated by the following Examples, of which certain are only included for comparative purposes:

EXAMPLE 1

Synthesis of a catalyst in accordance with the invention (i) Synthesis of the complexed titanium alkoxide precursor Two solutions are prepared: 10.01 g (0.1 mol) of acetylacetone (acac) are dissolved in 10 ml of isopropanol and separately 28.43 g (0.1 mol) of tetraisopropyl orthotitanate are dissolved in 30 ml of isopropanol. The two solutions are combined and, after mixing, the combined solution, in which the tetraisopropyl orthotitanate:acac molar ratio is 1:1, is heated at reflux temperature (110° C.) for 1 hour. Subsequently, the mixture is cooled to room temperature and as much solvent as possible is evaporated off at about 25° C. under a reduced pressure of about 100 mbar for 16 hours, whereafter a transparent yellowish liquid, which still contains isopropanol, remains behind. In this manner there are obtained about 68 g of acac-complexed tetraisopropyl orthotitanate which still contains a large amount of isopropanol.

(ii-a) Hydrolysis and sol production (without pre-hydrolysis of the silicon alkoxide)

19.1 g (0.028 mol) of acac-complexed tetraisopropyl orthotitanate [produced as described above in (i)] and 22.8 g (0.15 mol) of tetramethoxysilane are dissolved in 22 ml of isopropanol. A "hydrolysant", consisting of 15.0 ml (0.83 mol) of distilled water, 1.33 ml of hydrochloric acid (37 wt. %:0.016 mol HCl) and 15 ml of isopropanol, is added dropwise to the solution within 1 minute while stirring vigorously. 5 minutes after the addition a further 84 ml of isopropanol are added. Gelling can take place to some extent prior to use in the next process step.

(ii-b) Hydrolysis and sol production (with pre-hydrolysis of the silicon alkoxide)

22.8 g (0.15 mol) of tetramethoxysilane are dissolved in 22 ml of isopropanol and a "hydrolysant", consisting of 4.4 ml (0.24 mol) of distilled water, 1.33 ml of hydrochloric acid (37 wt. %:0.016 mol HCl) and 6 ml of isopropanol, is added dropwise to the resulting solution within 1 minute while stirring vigorously. The solution is heated to 50° C. and stirred at this temperature for 45 minutes.

After cooling the solution (in which the "pre-hydrolysis" of the tetramethoxysilane is effected) to room temperature 19.1 g (0.028 mol) of acac-complexed tetraisopropyl orthotitanate [produced as described above in (i)] are added to this solution. After 10 minutes a further 10.6 ml (0.59 mol) of distilled water in 9.5 ml of isopropanol are added. Finally, a further 84 ml of isopropanol are added to the solution. Gelling can take place to some extent prior to use in the next process step.

(iii) (Remaining) gelling and ageing

A steady, constantly dried nitrogen stream is allowed to flow for 48 hours at a flow velocity of 120 ml/min. over the sol or the at least partially gelled sol of process step (ii-a) or (ii-b) while stirring at room temperature. During this period not only the gelling but also the ageing takes place, and after the given period the gel is aged sufficiently.

(iv) Drying (extraction) with super-critical carbon dioxide

The aged gel of process step (iii) is introduced into a 2 l autoclave, this is sealed and carbon dioxide is conducted in at a temperature of 40° C. and a pre-pressure of 300 bar in the autoclave. After 2.3 kg of carbon dioxide have been conducted in over 1 hour the required pressure for the extraction of 240 bar at 40° C. in the autoclave and the filling of the separator is achieved. Thereafter, a further 6 kg of carbon dioxide at 40° C. and 240 bar are conducted for 5 hours with a flow velocity of 20 g/min. through the aged gel in the autoclave, during which the content of the autoclave is stirred with a turbine stirrer at only 60 r/min. in order to avoid settlement of the solid. The subsequent pressure reduction, in which the temperature is held at 40° C. and 20 g of carbon dioxide/min. are released, lasts approximately 2 hours. After completion of the reduction the mixture is cooled to room temperature and the resulting aerogel is separated and pounded.

The aerogel can already be used as a catalyst in this condition (without subsequent calcination).

(v) Calcination (with pre-treatment)

In the subsequent (optional) calcination the aerogel is first pre-treated for 1 hour in a U-tube reactor in a dry nitrogen stream having a velocity of 500 ml/min. at 200° C. (in the case of a subsequent calcination at 200° C.) or 400° C. (calcination at higher temperatures). The heating-up rate is 5° C./min.

After the pre-treatment the aerogel is cooled to below 80° C. and subsequently heated up at a rate of 5° C./min. to the desired calcination temperature in a dry stream of air of 500 ml/min. and held for 5 hours at this temperature (200° C., 400° C. or 600° C.). Thereafter, it is cooled to room temperature.

The calcinated aerogel can be used as a catalyst.

COMPARATIVE EXAMPLE B1

Synthesis of a titania-on-silica catalyst according to the method described in Example VII of U.S. Pat. No. 3,923,843

10 g of commercially available silica (Aerosil® 200, Degussa) are treated with a solution of 0.88 g of tetraisopropyl orthotitanate and 0.66 g of acetylacetone in 8.5 ml of isopropanol. The resulting impregnated silica gel is then dried at 500° C. for 3 hours in a nitrogen stream. Subsequently, air is allowed to enter into the reaction vessel and the temperature is allowed to rise to 800° C. Thereby, residual carbon is burnt and the silica is combined chemically with the titania. After 4 hours under these conditions the thus-produced titania-on-silica catalyst is cooled to room temperature [denoted hereinafter as catalyst B1). Analysis gives a titanium content of 1.5 wt. %.

COMPARATIVE EXAMPLES B2–B4

Synthesis of a titania-on-silica catalyst according to a method based on Example VII of U.S. Pat. No. 3,923,843

10 g of commercially available silica (Aerosil® 200, Degussa) are each treated with a solution of 1.2 g or 2.75 g or 11 g of tetraisopropyl orthotitanate and 0.85 g, 1.9 g or 7.6 g, respectively, of acetylacetone in 12 ml, 170 ml or 170 ml, respectively, of isopropanol. After heating at 60° C. for 5 hours the mixture is filtered and the thus-isolated impregnated silica gel is subsequently calcinated in each case at 600° C. or 800° C. for 4 hours in air. Finally, each of the thus-produced titania-on-silica catalysts B2 (600° C.), B2 (800° C.), B3 (600° C.), B3 (800° C.), B4 (600° C.) and B4 (800° C.) is cooled to room temperature. Analysis gives a titanium content of 1.0 wt. % (both B2's), 2.0 wt. % (both B3's) and 2.3 wt. % (both B4's).

COMPARATIVE EXAMPLE B5

Synthesis of a titania-on-silica catalyst according to a method based on Example VII on U.S. Pat. No. 3,923,843

12.6 g of commercially available silica (Aerosil® 200, Degussa) are treated with 1.42 g of titanium tetrachloride in 24 ml of methanol. After heating at 60° C. for 5 hours the resulting impregnated silica is dried at 100° C. and subsequently calcinated in air for 4 hours at 600° C. or 800° C. Finally, each of the thus-produced titania-on-silica catalysts B5 (600° C.) and B5 (800° C.) is cooled to room temperature. Analysis gives a titanium content of 2.6 wt. % in both cases.

EXAMPLE 2

Use of the catalysts of Example 1 and B1–5

Most of the catalysts exemplified in Examples 1 and B1–5 are used to catalyze the epoxidation of cyclohexene, in each case by reacting 6.3 g of pre-distilled cyclohexene with 15.9 ml of a 12 percent (wt./wt.) solution of cumene hydroperoxide in pre-distilled cumene in the presence of 0.1 g of catalyst. The reaction is carried out under argon at 60° C. in a closed 100 ml glass reactor fitted with a reflux condenser, thermometer, septum and dropping funnel. The argon serves to exclude oxygen and moisture as much as possible (previously, i.e. prior to the reaction, air and moisture are removed from the system using an argon stream as well as a vacuum pump). During the dropwise addition, effected through the dropping funnel, of the solution of cumene hydroperoxide in cumene to the sludge-like mixture of catalyst in cyclohexene present in the reactor the constantly stirred reaction mixture is held at 60° C.±0.5° C. using a bath provided with a thermostat.

The course of the reaction is followed by conventional analytical methods: samples of the reaction mixture are removed at regular intervals, they are filtered and the filtrate is analyzed by gas chromatography in order to determine the degree of epoxide formation. For this purpose there is used a HP 5890 gas chromatograph which is provided with an autosampler, a flame ionization detector and a capillary column HP-1 (50 m×0.32 mm×1.05 μm). In the automatic injection the injection temperature is 40° C., i.e. lower than the reaction temperature in order to avoid undesired reactions.

After completion of the reaction has been determined toluene is added to the mixture (suspension) and the yield of epoxide as well as the olefin conversion is evaluated quantitatively. Moreover, the hydroperoxide conversion is evaluated by iodometric titration using a Metrohm 686 titroprocessor.

The epoxidation and analysis carried out in the above manner is repeated three times in order to calculate the standard deviation. Based on the various results this is a maximum of ±2%.

The selectivities (S) acertained in the epoxidation experiments carried out a total of four times are calculated according to the following equations:

$$S_{hydroperoxide} (\%) = 100 \cdot [epoxide]_f / ([hydroperoxide]_i - [hydroperoxide]_f)$$

$$S_{olefin} (\%) = 100 \cdot [epoxide]_f / ([olefin]_i - [olefin]_f)$$

in which the concentrations ([ ]) are molar and the letters i and f denote the initial and final values, respectively.

The results of the tests described above are given in Table 1 hereinafter:

The results given above show that the catalyst manufactured according to Example 1 is at least about twice as active in the epoxidation of cyclohexene than the conventional catalysts produced according to Examples B1–5 by impregnating a silica carrier with a titanium-containing solution, this with the same or higher selectivity: the reaction time to 75 percent hydroperoxide conversion is in the case of the catalysts of Example 1 namely 29–36 minutes, in the case of the catalysts of Examples B1–B5 67–134 minutes. In comparison to the catalyst prepared according to the method described in Example VII of U.S. Pat. No. 3,923,843 (Example B1 in this description), the uncalcinated catalyst manufactured according to Example 1 shows even a more than four times higher activity with an about 6% higher epoxidation selectivity with respect to the hydroperoxide.

EXAMPLE 3

Use of the catalysts of Examples 1 and B1–5

Some of the catalysts exemplified in Examples 1 and B1–5 are used analogously to the method described in detail in Example 2 to catalyze the epoxidation of various olefins by reacting 60 mmol of the respective olefin with 15.9 ml of a 12 percent solution of cumene hydroperoxide in cumene in the presence of 0.1 g of catalyst. The reaction is carried out at 90° C. in a 100 ml glass reactor and the course is followed by conventional analytical methods. The results are given in Table 2 hereinafter:

TABLE 2

| Catalyst (of Example) | Substrate (olefin) | Reaction time to 50 percent hydroperoxide conversion | Reaction time to 95 percent hydroperoxide conversion | Epoxidation selectivity with respect to hydroperoxide |
|---|---|---|---|---|
| 1, uncalcinated | Cyclohexene | 3.4 min. | 10 min. | 93% |
| 1, uncalcinated | Norbornene | 7 min. | 59 min. | 88% |
| 1, uncalcinated | Limonene | 7 min. | 21 min. | 87% |
| B1 (800° C.) | Cyclohexene | 13 min. | 35 min. | 86% |
| B1 (800° C.) | Norbornene | 21 min. | 152 min. | 85% |
| B1 (800° C.) | Limonene | 19 min. | 64 min. | 81% |
| B3 (600° C.) | Cyclohexene | 5 min. | 15 min. | 88% |
| B3 (600° C.) | Norbornene | 9 min. | 70 min. | 89% |
| B3 (600° C.) | Limonene | 9 min. | 26 min. | 85% |

TABLE 1

| Catalyst (of Example) | Reaction time to 75 percent hydroperoxide conversion | Epoxidation selectivity with respect to hydroperoxide | Epoxidation selectivity with respect to cyclohexene |
|---|---|---|---|
| 1, uncalcinated | 29 min. | 93% | 99% |
| 1 (200° C.) | 33 min. | 92% | " |
| 1 (400° C.) | 36 min. | 92% | " |
| 1 (600° C.) | 35 min. | 93% | " |
| B1 (800° C.) | 134 min. | 87% | " |
| B2 (600° C.) | 72 min. | 93% | " |
| B2 (800° C.) | 93 min. | 92% | " |
| B3 (600° C.) | 67 min. | 88% | " |
| B4 (600° C.) | 79 min. | 85% | " |
| B5 (600° C.) | 89 min. | 81% | " |

The results given above show that in the epoxidation of larger olefins, such as norbornene and limonene, as well the uncalcinated catalyst manufactured according to Example 1 has a higher activity with the same or higher selectivity than the conventional catalysts produced according to Examples B1 and B3. These are good indications that the catalysts in accordance with the invention are excellent for oxidations in fine chemistry.

We claim:

1. A method for making a silica-titania mixed oxide aerogel catalyst which comprises:

1) hydrolyzing a silicon alkoxide and a titanium alkoxide-chelate complex wherein the molar ratio of silicon:titanium is in the range from about 1:1 to about 70:1 dispersed in a $C_{1-4}$-alkanol under acidic hydrolysis conditions using hydrochloric acid to obtain a silicon hydroxide and a titanium hydroxide;

2) condensing the silicon hydroxide and the titanium hydroxide to obtain a sol which contains oligomers having Si—O—Ti bonds, and water;
3) stirring the sol while exposing the sol to a dry inert gas to age and gel the sol; and
4) drying the aged and gelled sol by extracting the $C_{1-4}$ alkanol and the water with supercritical $CO_2$ whereby said silica-titania mixed oxide aerogel catalyst is obtained.

2. The method of claim 1 wherein the molar ratio of silicon:titanium is in the range from about 3:1 to about 12:1.

3. The method of claim 1 wherein the silicon alkoxide is of the formula $Si(OR^2)_4$ wherein $R^2$ is $C_{1-4}$ alkyl, and the titanium alkoxide-chelate complex is a titanium alkoxide of the formula $Ti(OR^1)_4$ wherein $R^1$ is $C_{1-4}$-alkyl complexed with acetylacetone.

4. The method of claim 3 wherein the titanium alkoxide is tetraisopropyl orthotitanate.

5. The method of claim 1 wherein the extraction with supercritical $CO_2$ is carried out at a temperature in the range from about 30° C. to about 50° C. and at a pressure in the range from about 200 bar to about 270 bar.

6. The method of claim 5 wherein the extraction with supercritical $CO_2$ is carried out at a temperature in the range from about 35° C. to about 40° C.

7. A method for making a silica-titanium mixed oxide aerogel catalyst which comprises:
1) hydrolyzing a silicon alkoxide dispersed in a $C_{1-4}$-alkanol under acidic hydrolysis conditions using hydrochloric acid to obtain a silicon hydroxide;
2) hydrolyzing a titanium alkoxide-chelate complex dispersed in a $C_{1-4}$-alkanol which alkanol further contains dispersed therein the silicon hydroxide wherein the molar ratio of silicon:titanium is in the range from about 1:1 to about 70:1 under acidic hydrolysis conditions using hydrochloric acid to obtain a titanium hydroxide dispersed with the silicon hydroxide;
3) condensing the silicon hydroxide and the titanium hydroxide to obtain a sol which contains oligomers having Si—O—Ti bonds, and water;
4) stirring the sol while exposing the sol to a dry inert gas to age the sol; and
5) drying the aged and gelled sol by extracting the $C_{1-4}$-alkanol and the water with supercritical $CO_2$ whereby said silica-titania mixed oxide aerogel catalyst is obtained.

8. The method of claim 7 wherein the molar ratio of silicon:titanium is in the range from about 3:1 to about 12:1.

9. The method of claim 7 wherein the silicon alkoxide is of the formula $Si(OR^2)_4$ wherein $R^2$ is $C_{1-4}$ alkyl, and the titanium alkoxide-chelate complex is a titanium alkoxide of the formula $Ti(OR^1)_4$ wherein $R^1$ is $C_{1-4}$-alkyl complexed with acetylacetone.

10. The method of claim 9 wherein the titanium alkoxide is tetraisopropyl orthotitanate.

11. The method of claim 7 wherein the extraction with supercritical $CO_2$ is carried out at a temperature in the range from about 30° C. to about 50° C. and at a pressure in the range from about 200 bar to about 270 bar.

12. The method of claim 11 wherein the extraction with supercritical $CO_2$ is carried out at a temperature in the range from about 35° C. to about 40° C.

* * * * *

UNITED STATES PATENT AND TRADEMARK OFFICE
CERTIFICATE OF CORRECTION

PATENT NO  : 5,935,895

DATED      : Ausgust 10, 1999

INVENTOR(S) : Alfons Baiker, Dominique Dutoit, Remo Hutter

It is certified that error appears in the above-identified patent and that said Letters Patent are hereby corrected as shown below:

Claim 5, column 11, line 21, change "30°" to --31°--.

Signed and Sealed this

Eighth Day of February, 2000

*Attest:*

Q. TODD DICKINSON

*Attesting Officer*     *Commissioner of Patents and Trademarks*